(12) United States Patent
Giese et al.

(10) Patent No.: US 10,429,176 B2
(45) Date of Patent: Oct. 1, 2019

(54) PIPELINE DEEP CRACK DETECTION

(71) Applicant: General Electric Company, Schenectady, NY (US)

(72) Inventors: Jochen Uwe Giese, Karlsruhe (DE); Olaf Mueller, Bad Bergzabern (DE)

(73) Assignee: General Electric Company, Schenectady, NY (US)

(*) Notice: Subject to any disclaimer, the term of this patent is extended or adjusted under 35 U.S.C. 154(b) by 173 days.

(21) Appl. No.: 15/617,632

(22) Filed: Jun. 8, 2017

(65) Prior Publication Data

US 2018/0356371 A1 Dec. 13, 2018

(51) Int. Cl.
*G01N 29/44* (2006.01)
*G01B 17/02* (2006.01)
(Continued)

(52) U.S. Cl.
CPC ........... *G01B 17/02* (2013.01); *G01N 29/043* (2013.01); *G01N 29/225* (2013.01);
(Continued)

(58) Field of Classification Search
CPC .. G01N 29/4445; G01N 29/043; G01N 29/44; G01N 29/225; G01N 29/265;
(Continued)

(56) References Cited

U.S. PATENT DOCUMENTS 2,795,133 A 6/1957 Ots
4,112,850 A 9/1978 Sigel-Gfeller
(Continued)

FOREIGN PATENT DOCUMENTS

CA 1169541 A1 6/1984
WO 1981002636 A1 9/1981
(Continued)

OTHER PUBLICATIONS

CyberLogic; "Ultrasound detecting a crack in an oil pipeline using computer simulation;" Retrieved from the Internet at http://www.cyberlogic.org/pipeline.html; 2015.
(Continued)

*Primary Examiner* — Natalie Huls
*Assistant Examiner* — Suman K Nath
(74) *Attorney, Agent, or Firm* — Mintz Levin Cohn Ferris Glovsky and Popeo, P.C.

(57) ABSTRACT

A pipeline inspection system includes a pipeline pig having a controller and a plurality of ultrasonic transducer elements situated in an array. Each of the plurality of ultrasonic transducer elements emits an ultrasonic signal into a wall of a pipeline and receives echoes of the ultrasonic signal from the pipeline wall. The controller selects a first subset of the plurality of ultrasonic transducer elements from which to emit the ultrasonic signals into the wall of the pipeline as the pipeline pig passes through the pipeline, analyzes the echoes of the ultrasonic signals received by the plurality of ultrasonic transducer elements to detect a feature in the pipeline wall, and selects a second subset of the plurality of ultrasonic transducer elements to emit the ultrasonic signals into the wall of the pipeline as the pipeline pig passes through the pipeline when the feature is detected in the pipeline wall.

17 Claims, 6 Drawing Sheets

(51) Int. Cl.
*G01N 29/04* (2006.01)
*G01N 29/22* (2006.01)
*G01N 29/26* (2006.01)
*G01N 29/48* (2006.01)

(52) U.S. Cl.
CPC ....... *G01N 29/262* (2013.01); *G01N 29/4427* (2013.01); *G01N 29/48* (2013.01); *G01N 2291/02854* (2013.01); *G01N 2291/044* (2013.01); *G01N 2291/106* (2013.01); *G01N 2291/2636* (2013.01)

(58) Field of Classification Search
CPC ....... G01N 2291/044; G01N 2291/106; G01N 2291/2636; G01B 17/02; G01M 3/005; G01M 3/246; F16L 55/26; F17D 5/06
USPC ......... 73/579, 623, 620, 622, 625, 626, 627, 73/638, 640
See application file for complete search history.

(56) References Cited

U.S. PATENT DOCUMENTS

| | | | |
|---|---|---|---|
| 4,573,231 | A | 3/1986 | Stocksiefen et al. |
| 6,023,986 | A | 2/2000 | Smith et al. |
| 6,190,090 | B1 | 2/2001 | Campbell et al. |
| 6,571,634 | B1 | 6/2003 | Bazarov et al. |
| 6,578,422 | B2 | 6/2003 | Lam et al. |
| 6,745,136 | B2 | 6/2004 | Lam et al. |
| 6,848,313 | B2 | 2/2005 | Krieg et al. |
| 7,240,554 | B2 | 7/2007 | Berke |
| 7,299,697 | B2 | 11/2007 | Siddu et al. |
| 7,997,139 | B2 | 8/2011 | Owens et al. |
| 8,042,399 | B2 | 10/2011 | Pasquali et al. |
| 8,390,278 | B2 | 3/2013 | Petrosky |
| 8,776,558 | B2 | 7/2014 | Volker |
| 9,404,903 | B2* | 8/2016 | Batzinger ............... G01N 33/00 |
| 9,632,062 | B2* | 4/2017 | Tanaka ................. G01N 29/043 |
| 10,036,680 | B2* | 7/2018 | Frueh .................... G01M 3/005 |
| 10,060,883 | B2 | 8/2018 | Giese et al. |
| 2007/0023096 | A1 | 2/2007 | Buckley et al. |
| 2009/0078049 | A1 | 3/2009 | Sinha |
| 2009/0158850 | A1 | 6/2009 | Alleyne et al. |
| 2011/0296923 | A1* | 12/2011 | Cataldo ................ G01N 29/043 73/632 |
| 2014/0153368 | A1 | 6/2014 | Bar-Cohen et al. |
| 2015/0338378 | A1 | 11/2015 | Lu |

FOREIGN PATENT DOCUMENTS

| | | |
|---|---|---|
| WO | 2004097397 A1 | 11/2004 |
| WO | 2016/137335 A1 | 9/2016 |

OTHER PUBLICATIONS

Vogel et al; "Ultrasound tool can combine metal loss and crack inspection of gas pipelines;" Pipeline & Gas Journal234.8; Aug. 2007.

Falck, C., Svendsen, C., and O'Donoghue, A.; "Multi diameter pigging for Asgard;" ;IBC's Annual 23rd Event Offshore Pipeline Tech; Feb. 28, 2000.

Lindner, H., Beuker, T., and Diekamp, M.; "In-Line Inspection of Multi-Diameter Pipelines: Standardized Development and Testing for a Highly Efficient Tool Fleet;" ROSEN Technology & Research Center, Feb. 28, 2011.

Beuker, T., Brockhaus, S., and Lindner, H.; "Overcoming the specific issues associated with the in-line inspection of gas pipelines:" PPSA Seminar; Dec. 16, 2010.

Bluck, M.; "How to develop and deliver thick wall multi-diameter offshore inspection solutions: A case study;" Annual Technical Seminar of the PPSA; Nov. 14, 2012.

Dr. Roye, W.I., "Advanced Phased Array Technologies", 3CNEND— 3a Conferencia Nacional em Ensaios Nao Destrutivos, Retrieved from the Internet URL: https://www.karldeutsch.de/PDF/PAUT/Roye%20Advanced%20Phased%20Array%20Techniques.pdf, pp. 1-8, (Dec. 15-16, 2014).

Hirasawa, T. et al., "Basic Study on the Phased Array UT Technique for Crack Depth Sizing in Ni-Based Alloy Weld" E-Journal of Advanced Maintenance, vol. 5-2, pp. 146-154, (2013).

Nardoni, G., et al., "Sizing the Height of Discontinuities, Their Characterisation in Planar / Volumetric by Phased Array Technique Based on Diffracted Echoes", Retrieved from the Internet URL: http://www.idspektr.ru/10_ECNDT/reports/1_03_02.pdf, pp. 1-11, (Oct. 24, 2018).

International Search Report and Written Opinion issued in connection with corresponding PCT Application No. PCT/US2018/027464 dated Jul. 30, 2018.

* cited by examiner

PIPELINE DEEP CRACK DETECTION

BACKGROUND

A pipeline inspection gage or "pig" is a tool directed through a section of pipeline, typically advanced through the pipeline by the pressure of fluid flow through the pipeline, or other differences in pressure within the pipeline. Pigs may be used to inspect the pipeline with various sensors, to separate fluid flows within the pipeline, to clean the interior surface of the pipeline, to record geometric information about the pipeline, as well as for other purposes. One way to inspect the pipeline is to pass a sensor-carrying pig module (e.g., sensor carrier module) through the pipeline. Transducers mounted to the pipeline pig may be configured to emit ultrasonic signals into the pipeline wall and receive reflected ultrasonic signals, which may be analyzed or processed to detect features (e.g., cracks) in the pipeline.

BRIEF DESCRIPTION

In pipeline inspection, it would be beneficial to develop techniques for determining the depth of features, such as deep features, in the wall of the pipeline. Several embodiments of the disclosed subject matter are summarized below. These embodiments are not intended to limit the scope of the disclosed subject matter, but rather are intended only to provide a brief summary of possible forms of the disclosed subject matter. Indeed, the disclosed subject matter may encompass a variety of forms that may be similar to or different from the embodiments set forth below.

In a first embodiment, an ultrasonic pipeline inspection system includes a pipeline pig. The pipeline pig includes a plurality of ultrasonic transducer elements situated in an array and a controller. Each of the plurality of ultrasonic transducer elements is configured to emit an ultrasonic signal into a wall of a pipeline and to receive echoes of the ultrasonic signal from the pipeline wall. The controller is configured to select a first subset of the plurality of ultrasonic transducer elements from which to emit the ultrasonic signals into the wall of the pipeline as the pipeline pig passes through the pipeline, analyze the echoes of the ultrasonic signals received by the plurality of ultrasonic transducer elements to detect a feature in the pipeline wall, and select a second subset of the plurality of ultrasonic transducer elements to emit the ultrasonic signals into the wall of the pipeline as the pipeline pig passes through the pipeline when the feature is detected in the pipeline wall.

In a second embodiment, a method includes directing a plurality of ultrasonic transducer elements situated in an array along a wall of a pipeline, emitting a first ultrasonic signal from a first subset of the plurality of ultrasonic transducer elements, receiving echoes of the first ultrasonic signal from the pipeline wall, analyzing the echoes of the first ultrasonic signal to detect a feature in the pipeline wall, emitting a second ultrasonic signal from a second subset of the plurality of ultrasonic transducer elements, and analyzing the echoes of the second ultrasonic signal to determine a depth of the feature in the pipeline wall.

In a third embodiment, a non-transitory computer readable medium includes executable instructions that when executed cause a processor to select a first subset of a plurality of ultrasonic transducer elements situated in an array, wherein the first subset of the plurality of ultrasonic transducer elements are configured to emit a first ultrasonic signal into a wall of a pipeline and to receive echoes of the first ultrasonic signal from the pipeline wall, analyze the echoes of the first ultrasonic signal received by the first subset of the plurality of ultrasonic transducer elements to detect a feature in the pipeline wall, select a second subset of the plurality of ultrasonic transducer elements, wherein the second subset of the plurality of ultrasonic transducer elements are configured to emit a second ultrasonic signal into the wall of the pipeline and to receive echoes of the second ultrasonic signal from the pipeline wall, and analyze the echoes of the second ultrasonic signal to determine a depth of the feature in the pipeline wall.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

One or more specific embodiments of the disclosed subject matter will be described below.

The subject matter disclosed herein relates to inspecting fluid pipelines, and more specifically, to using ultrasonic transducers to identify characteristics (e.g., depth) of detected features (e.g., cracks).

A pipeline may be inspected by passing a pipeline pig with a sensor carrier module through the pipeline. The sensor carrier may be equipped with arrays (e.g., phased arrays) of ultrasonic transducer elements, piezo ultrasonic transducers, piezocomposite ultrasonic transducers, electromagnetic acoustic transducers (EMATs), magnetic flux sensors, etc. which may be mounted to skids that slide along the interior surface of the pipeline. The sensors may be used to detect the presence and depth of cracks, corrosion, or other features, measure wall-thickness, or otherwise determine the condition of the pipeline.

For example, a plurality of transducer elements may emit an ultrasonic signal and receive reflected ultrasonic signals that have been reflected by the pipeline wall. Echoes in the reflected ultrasonic signals may be indicative of a crack or other features in the pipeline wall. In some instances, the received reflected ultrasonic signals may be analyzed to determine whether a feature exceeds a threshold depth, but not the depth that a feature extends into the wall. Using a system with an array of transducer elements, the effective transducer width may be adjusted by utilizing various numbers (e.g., subsets) of the available transducer elements within the array. By utilizing a subset of the transducer elements of the array of transducer elements on each skid as the pig 10 moves through the pipeline, the effective transducer width may be dynamically adjusted to effectuate adjustment of the coverage areas in which a feature is detected. Using the techniques described herein, analysis of the reflected ultrasonic signals collected by the transducer elements may be used to determine the presence of a feature in the pipeline, and can also be used to determine one or more characteristics (e.g., depth) of the feature. Accordingly, the disclosed techniques may be used to give a user or system a more complete understanding of the condition of a length of pipeline.

Figure 1:
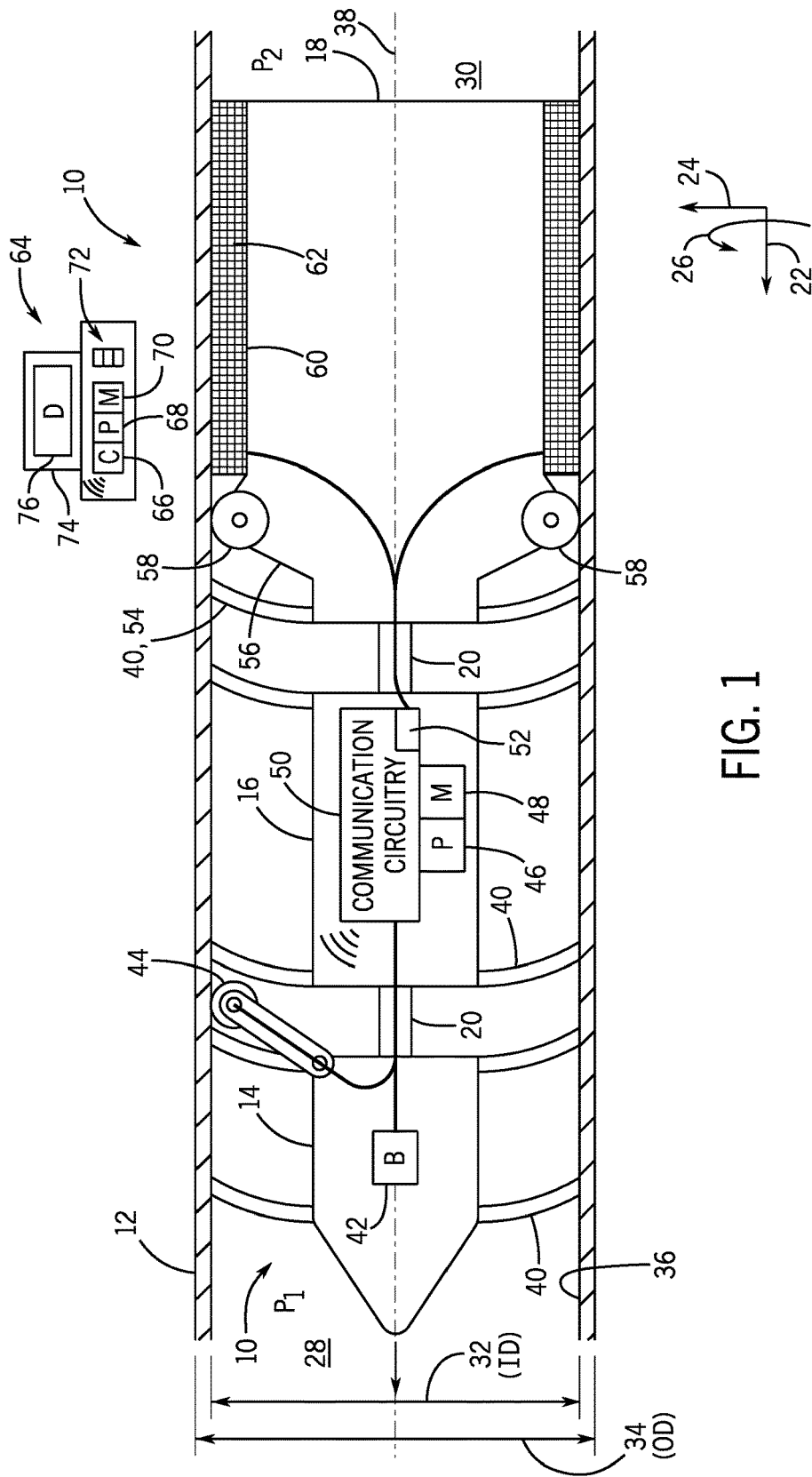
FIG. 1 is a cross-sectional schematic of an embodiment of an exemplary pipeline pig with a sensor carrier module inside a pipeline.

Turning now to the figures, FIG. 1 is a cross-sectional schematic of an exemplary embodiment of a pipeline pig 10 inside a pipeline 12, which may include one or more of a tow (or battery) module 14, a control module 16, and a sensor carrier module 18, connected by linkages 20. For clarity, an axial direction 22, a radial direction 24, and a circumferential direction 26 are shown in FIG. 1 though directions may vary. The pipeline 12 may have a downstream end 28 (i.e., in the direction of travel), an upstream end 30 (i.e., opposite the direction of travel), an inside diameter 32, an outside diameter 34, and an interior surface 36 (e.g., cylinder interior surface). The pig 10 may have a pig axis 38, which may be substantially aligned with an axis of the pipeline 12.

One or more, or each module 14, 16, 18, may have one or more sealing/support members 40 configured to create a seal between the respective module 14, 16, 18 and the interior surface 36 of the pipeline 12, as well as to provide support for, and center, the respective module 14, 16, 18 in the pipe. Each of the sealing members 40 may reduce or eliminate fluid flow from one side of the sealing member 40 to the other. In some embodiments, the seals created by sealing members 40 may allow for some fluid flow or some pressure equalization. By sufficiently restricting fluid flow, rather than stopping all fluid flow, the sealing members 40 may achieve their purpose. Each sealing member 40 may be an annular seal structure, which may project or protrude radially outward from the module 14, 16, 18 toward the interior surface 36. The sealing member 40 may include a flat disc-shaped annular seal structure, a first conical seal structure, a curved annular seal structure, or any combination thereof.

In the embodiment shown in FIG. 1, the tow module 14 is the first module in the pig 10. However, the order of modules 14, 16, 18 in the pig 10, and even which modules are included in the pig 10, may vary from embodiment to embodiment. That is, some embodiments of the pig 10 may include a scraping, brushing, cleaning, or attracting (e.g., magnetic) module in addition to a sensor carrier module 18. In some embodiments, the tow module 14 may include a battery 42 used to provide power for any components in the pig 10 such as sensors, processors, memory components, communication circuitry, drive components, pneumatics, hydraulics, etc. The tow module 14 or the control module 16 may include a measuring wheel 44, configured to measure the distance traveled by the pig 10 in the pipeline 12.

The tow module 14 may also include one or more sealing members 40 configured to create a seal between the tow module 14 and the interior surface 36 of the pipeline 12. The sealing members 40 may be made of any flexible material capable of forming a seal with the interior surface 36 of the pipeline 12. Though FIG. 1 shows one sealing member 40 toward the front of the tow module 14, and one sealing member toward the rear of the tow module 14, the tow module 14 may have any number of sealing members 40.

In the embodiment shown in FIG. 1, the control module 16 may follow the tow module 14. As previously discussed, the order of modules may differ among embodiments. The control module 16 may include a processor 46 for executing programs, processing data collected from sensors, and the like. The control module 16 may also include a memory 48 component (e.g., a non-transitory computer readable medium) in communication with the processor 46 that may be used to store data, programs, processing routines, instructions for the processor 46, sensor parameters, etc. The control module 16 may include communication circuitry 50 configured to communicate data from sensors to the processor 46 and memory 48. The communication circuitry 50 may communicate collected data to a user or some device wirelessly (e.g., WiFi, Bluetooth, ANT, ZigBee, near field communication, etc.) or through port 52 (e.g., USB, mini or micro USB, CAN, RS232, RS485, or other method of wired data transmission). Data analysis and/or communication may be in real time (i.e., as data is collected), near real time (e.g., within microseconds, milliseconds, seconds or tens of second from data being collected), or after the pig 10 has passed through a section of the pipeline 12.

As with the tow module 14, the control module 16 may include one or more sealing members 40 configured to create a seal between the control module 16, and the interior surface 36 of the pipeline 12, and to minimize fluid flow from one side of the sealing member 40 to the other. As with the tow module 14, the control module 16 may have 1, 2, 3, 4, 5, 6 or more sealing members 40.

In the embodiment shown in FIG. 1, the sensor carrier module 18 may follow the control module 16. The sensor carrier module 18, as with the tow module 14 and the control module 16, may have one or more sealing members 40 to create a seal between the sensor carrier module 18, and the interior surface 36 of the pipeline 12, and to minimize fluid flow from one side of the sealing member 40 to the other. The sealing member 40 may also be used to provide support for the sensor carrier module 18 and/or center the sensor carrier module 18 in the pipeline 12.

In the embodiment shown in FIG. 1, the leading sealing member 54 of the sensor carrier module 18 may be followed by a generally annular shaped flexible section 56. The flexible section 56 may be a flexible annular structure or assembly which is configured to expand and contract in the radial direction 24. For simplicity, the section may be described as a flexible cone section in the following discussion, though other shapes and configurations may be used. The cone section 56 may include a plurality of parts arranged in a conical shape or be made of a single monolithic piece.

A plurality of rotational guides 58 such as rollers, balls, or wheels may be attached to the cone section 56, disposed about the cone section 56 in the circumferential direction 26 such that the rotational guides 58 are in contact with the interior surface 36 of the pipeline 12, or separated from the interior surface 36 of the pipeline 12 by a thin film of fluid. Although the rotational guides 58 may be any rotational structure such as rollers, balls, or wheels, the following discussion refers to the rotational guides 58 as wheels for simplicity. However, it should be understood that the wheels 58 are intended to cover any rotational structure that helps to reduce friction. In some embodiments, the wheels 58 may be of any suitable shape such that they roll along the interior surface 36 of the pipeline 12 as the pig 10 and sensor carrier module 18 move through the pipeline 12. The illustrated embodiments may include any number of wheels 58. While this specification discusses rotational guides, other types of non-rotational guides that reduce friction are also possible.

The plurality of wheels 58 may be coupled to and may be followed by a plurality of slat-shaped skids 60 (e.g., axially extending skids), which may be disposed circumferentially about the interior surface 36 of the pipeline 12 such that the skids 60 are in contact with the interior surface 36 of the pipeline 12, or separated from the interior surface 36 of the pipeline 12 by a thin film of fluid (e.g., couplant medium). The skids 60 may include an array of sensors 62 (e.g., ultrasonic transducer elements) extending down the length of each skid 60.

In some embodiments, the sensors 62 may be recessed from the surface of the skid 60 such that the sensors are spaced within a desired distance from the interior surface 36 of the pipeline. In some embodiments, the sensor 62 may be placed at any distance between approximately 0 millimeters and 100 millimeters from the interior surface 36 of the pipeline 12, (e.g., 30 millimeters), although larger distances are possible.

In general, if the downstream 28 ends of the skids 60 remain in contact, or in near contact with the interior surface 36 of the pipeline, the sensors 62 maintain the desired spacing with the interior surface 36 of the pipeline. The sensors 62 may be any ultrasonic transducer (e.g., piezo ultrasonic transducers, piezocomposite ultrasonic transducers, etc.) configured to detect or size cracks in the pipeline 12, or any other kind of sensor which may be used to inspect a section of pipeline 12.

In the present embodiment shown in FIG. 1, the pig 10 may be propelled through a section of pipeline 12 by a difference between the pressure P1 ahead of the pig 10 and the pressure P2 behind the pig 10, as maintained by, for example, the plurality of sealing members 40. The pig 10 may pass through the section of pipeline 12 based upon the pressure of a fluid flowing through the pipeline 12 or based upon fluid pressure using a pump in an upstream direction 30 or downstream direction 28 of the pig. It should be understood, however, that other techniques for pushing, pulling, propelling, or otherwise passing the pig 10 through the section of pipeline 12 may be used. For example, the pig 10 may be pulled through the pipeline 12 using a cable, or the pig 10 may propel itself (e.g., with driven wheels, a conveyer belt like track, etc.) through the section of pipeline 12 using a motor or some other method.

Data collected using the pipeline pig 10 may be analyzed by the processor 46 of the control module 16, using an external computing device 64 (e.g., computer, tablet, mobile device, etc.), or a combination thereof. The computing device 64 may include communication circuitry 66, a processor 68, memory 70, communication ports 72, and a user interface 74, which may include a display 76. While the pipeline pig 10 is being passed through the pipeline 12 to take measurements, or following the pipeline pig 10 being passed through the pipeline 12, data may be passed to the computer 64 wirelessly or through a wired connection via communication ports 52, 72. The computer 64 may be located near the pipeline pig 10 or remote from the pipeline pig 10. In some embodiments (e.g., the computer 64 is located remotely relative to the pipeline pig 10), the data may be passed to the computer 64 via the cloud or over a network. In other embodiments, the computer 64 may be in wireless communication with the pipeline pig 10 while the pipeline pig 10 is traveling through the pipeline 12 and analyzing data in real time or near real time. The computer 64 may be outfitted with software stored on the memory component 70 and executed by the processor 68 to facilitate analysis of the collected data. For example, the computing device 64 may be capable of post-processing the data collected by the sensors (e.g., identifying echoes in the data, determining how the ultrasonic signals were reflected within the pipeline wall), and identify features in the pipeline wall, as well as additional characteristics (e.g., depth) of the identified features.

Though FIG. 1 shows one application of the disclosed techniques, using a pipeline pig 10 to inspect a pipeline 12, this is merely an example and not intended to limit the scope of the disclosed techniques. For example, the disclosed techniques may be used to identify the presence of and characteristics of one or more features in a wall 80, or any other piece of material using ultrasonic transducer elements.

Figure 2:
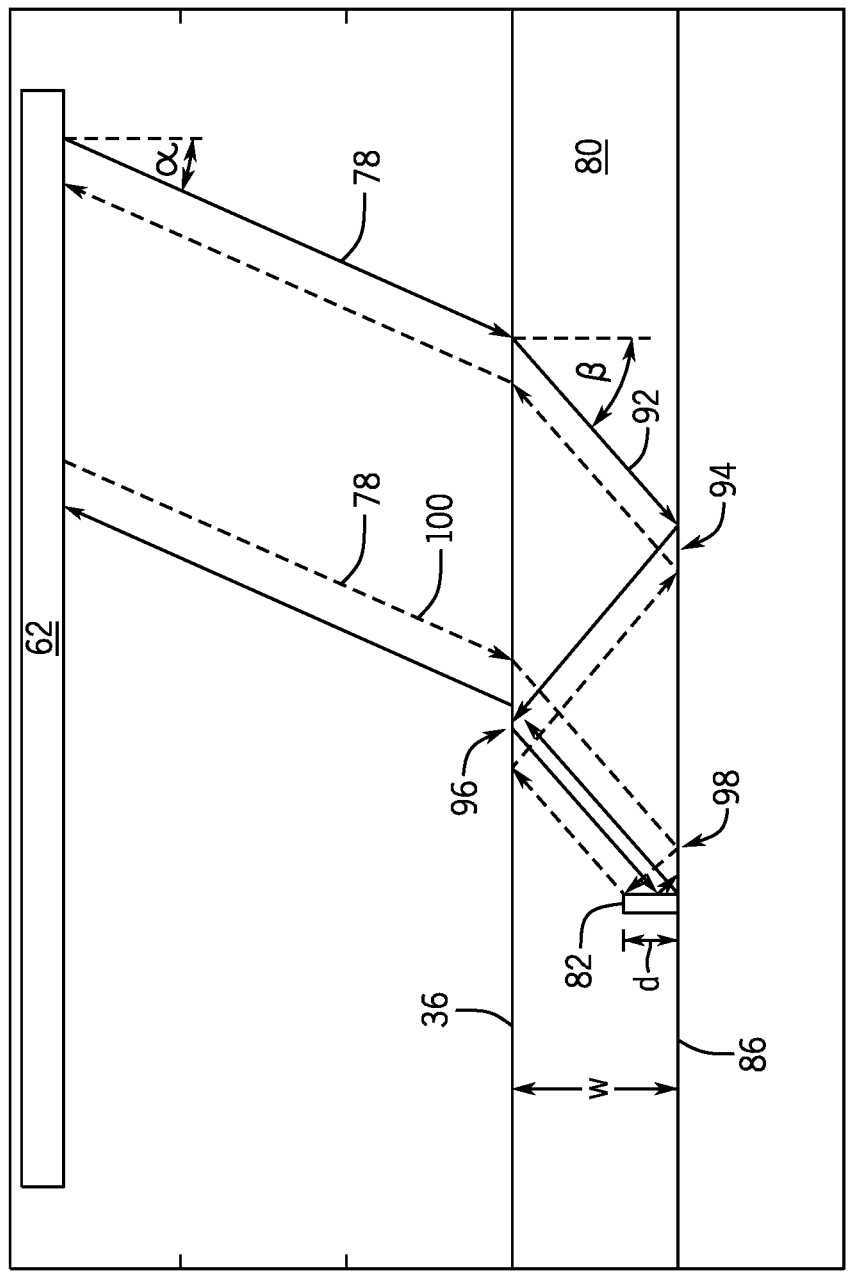
FIG. 2 shows a ray trace of one embodiment of a "one skip" ultrasonic signal echo within a wall of the pipeline of FIG. 1.

In operation, the pipeline pig 10 may transmit one or more ultrasonic signals. FIG. 2 shows a ray trace of a "one-skip" ultrasonic signal echo received by the sensors 62 that indicate a feature (e.g., a crack) in a piece of material. As part of the operation of the pipeline pig 10, an ultrasonic signal can be emitted from the transducer elements 62 and interacts with the interior surface 36 of the pipeline wall 80 and at an incidence angle, a. The ultrasonic signal 78 can be refracted and propagates through the pipeline wall 80 at a propagation angle, β. At least a portion of the ultrasonic signal 78 may then follow one of two paths. In some embodiments, in a first path 92 (indicated by the solid arrows), the ultrasonic signal 78 reflects off of an exterior surface 86 of the pipeline wall 80 at a first location 94, reflects off of the interior surface 36 of the pipeline wall 80 at a second location 96, reflects off of a feature 82, reflects off of the exterior surface 86 of the pipeline wall 80 at a third location 98, toward the interior surface 36 of the pipeline wall 80, then refracts back to the transducer elements 62. In a second path 100 (indicated by the dashed arrows), the ultrasonic signal 78 reflects off of the exterior surface 86 of the pipeline wall 80 at the third location 98, reflects off of the feature 82, reflects off of the interior surface 36 of the pipeline wall 80 at the second location 96, reflects off of the exterior surface 86 of the pipeline wall 80 at the first location 94, toward the interior surface 36 of the pipeline wall, then refracts back to the transducer elements 62.

Figure 3:
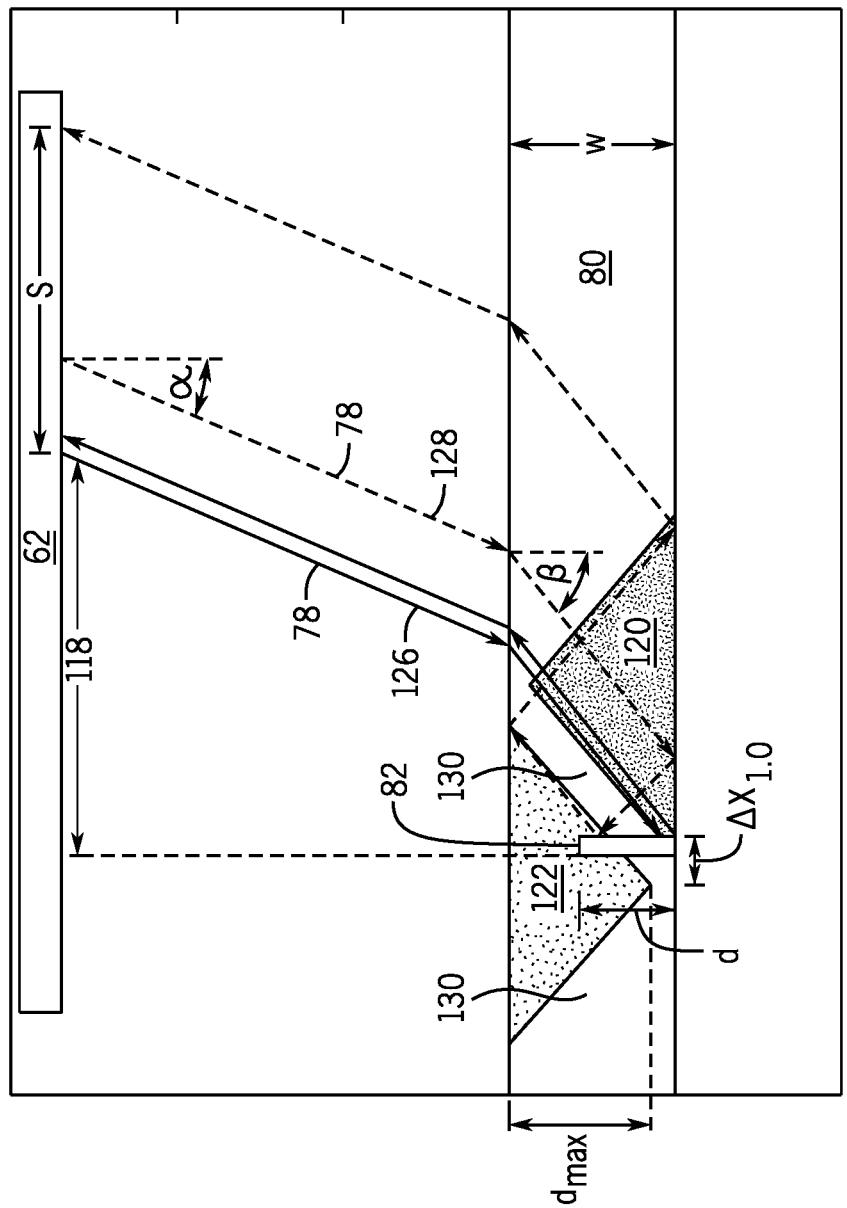
FIG. 3 is a schematic of one embodiment of coverage areas for transducer elements at a known position or distance from a feature within the pipeline of FIG. 1.

Using the ray trace of FIG. 2, coverage areas may be defined such that the sensor 62 can detect the feature 82 if it extends into one of the coverage areas. FIG. 3 is a schematic of one embodiment of the coverage areas for the transducer elements 62 at a known position 118 or distance from the feature 82. If the feature 82 is disposed within the first coverage area 120, as shown in FIG. 3, the ultrasonic transducer elements 62 at position 118 can detect an echo. Similarly, if the feature is disposed within the second coverage area 122, as shown in FIG. 3, the ultrasonic transducer elements 62 can also detect an echo. As described in more detail below, it is possible, and in some cases even expected, for the transducer elements 62 to receive multiple echoes. It should be noted that the spaces between coverage areas 120, 122, indicate areas that are not covered by the transducer elements 62. That is, a feature 82 disposed entirely in space 130 (i.e., the feature 82 does not extend into coverage areas 120, 122) may not be detected by the transducer elements because no echoes will be returned. However, because the sensor carrier module 18 of a pipeline pig 10 has multiple skids 60 disposed circumferentially 26 about the interior surface 36 of the pipeline, and each skid 60 has multiple sensors 62 situated in an array along the length of the skid, the size of space 130 can be reduced or effectively eliminated so that the feature 82 is likely to fall within the coverage areas 120, 122, 124 of the sensor 62 as it travels through the pipeline 12, or a neighboring sensor, or one of the many other sensors. Additionally, it should be understood that the sensors 62 may be arranged in order to minimize coverage gaps. Similarly, in some embodiments signals may be compared between sensors 62 to analyze sensed echoes.

The feature 82 may be disposed in more than one coverage area 120, 122. In such cases, the ultrasonic transducer elements 62 may receive multiple reflected ultrasonic signals indicative of multiple echoes. For example, in FIG. 3, the feature 82 is in the first coverage area 120 and the second coverage area 122. Thus, the ultrasonic transducer elements 62 will return two echoes (as indicated by the first ray trace 126 and the second ray trace 128 shown in FIG. 3). Indeed, the various combination of returned signals (e.g., echoes) may be used to determine the threshold depth (e.g., d) or minimum depth of the feature 82 based on which echoes are received (rather than the amplitudes of the received echoes).

As previously discussed, a second echo can appear if the feature 82 propagates from the exterior surface 86 of the pipeline wall 80 and falls within the second coverage area 122. That is, a second echo can appear if:

$$d \geq w - \frac{1}{\tan\beta}\left(\frac{s}{2\cos\alpha} - |\Delta x_2|\right), \quad (1)$$

Wherein d is the depth of the feature, w is the wall thickness of the pipeline, s is the width of the transducer elements 62 being utilized, a is the incidence angle of the ultrasonic signal, $\beta$ is the propagation angle of the ultrasonic signal through the pipeline wall 80, $d_{max}$ is the maximum depth of the coverage areas 120, 122, and $\Delta x_2$ is the distance of the feature 82 in the axial direction 22 from the center of the second coverage area 122. If the exact position of the feature 82 relative to the sensor 62 (e.g., $\Delta x_2$) is unknown, then a lower bound of d may be determined by setting $\Delta x_2$ to zero, such that:

$$d \geq w - \frac{s}{2\tan\beta\cos\alpha}. \quad (2)$$

If a second echo appears with a first echo, then the feature spans across the first coverage area 120 and the second coverage area 122 (as shown in FIG. 3). Thus:

$$|\Delta x| \geq w\tan\beta - \frac{s}{2\cos\alpha} \quad (3)$$

and thus, by substituting Equation 3 for $\Delta x$ in Equation 1 above:

$$d \geq 2w - \frac{s}{\tan\beta\cos\alpha}. \quad (4)$$

Thus, a first echo by itself indicates the presence of the feature 82. A second echo by itself indicates that:

$$d \geq w - \frac{s}{2\tan\beta\cos\alpha}. \quad (5)$$

A first echo and a second echo indicates that:

$$d \geq 2w - \frac{s}{\tan\beta\cos\alpha}. \quad (6)$$

Accordingly, based upon the presence of first and second echoes in the ultrasonic signal 78 received by the ultrasonic transducer elements 62, the threshold depth of the detected feature 82 may be determined. Though FIGS. 2 and 3 show a feature 82 propagating from the exterior surface 86 of the pipeline wall 80, Equation 6 holds true for features 82 propagating from the interior surface 36 of the pipeline wall 80. Equation 5 holds true for features 82 propagating from the interior surface 36 of the pipeline wall 80 if either a first echo is returned. It should be noted that these techniques allow for the determination of minimum or threshold feature depth based on the existence of echoes, rather than the amplitudes of the echoes. For example, the mere presence of a first echo and a second echo means that a feature is deep enough to span across the first coverage area 120 and the second coverage area 122, or vice versa. A second echo by itself means that a feature propagating from the exterior surface 86 of the pipeline wall 80 is deep enough to propagate into the second coverage area 122. In some embodiments, multiple readings from the transducer elements 62 as they pass through the pipeline 12 may be combined and/or compared to determine more about the feature 82 (e.g., position, a more detailed depth determination, etc.). Accordingly, by relying on the mere presence of an echo rather than the amplitude of the echo, data processing and set up (e.g., setting a threshold amplitude) is simplified and does not require evaluation of the echo amplitude.

Figure 4:
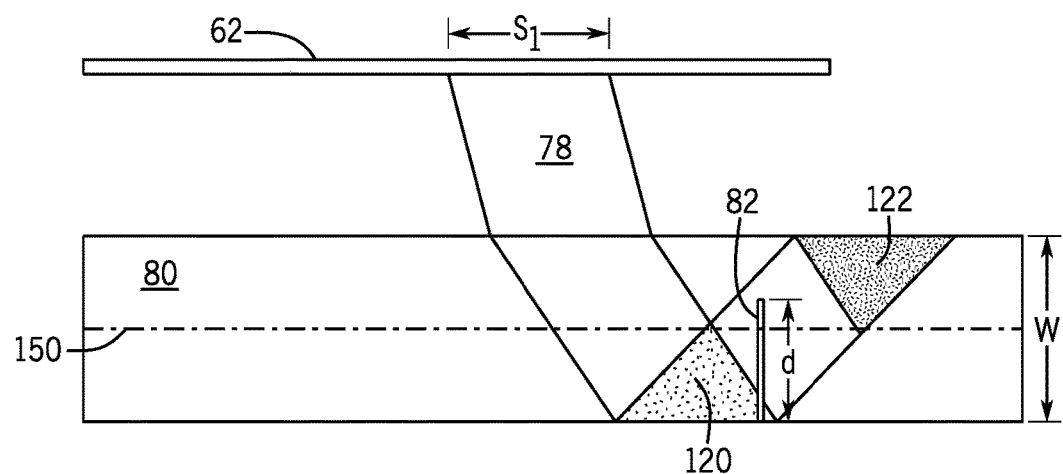
FIG. 4 is a schematic of one embodiment of the coverage areas for the transducer elements of FIG. 3 having a first effective width, $s_1$.
Figure 5:
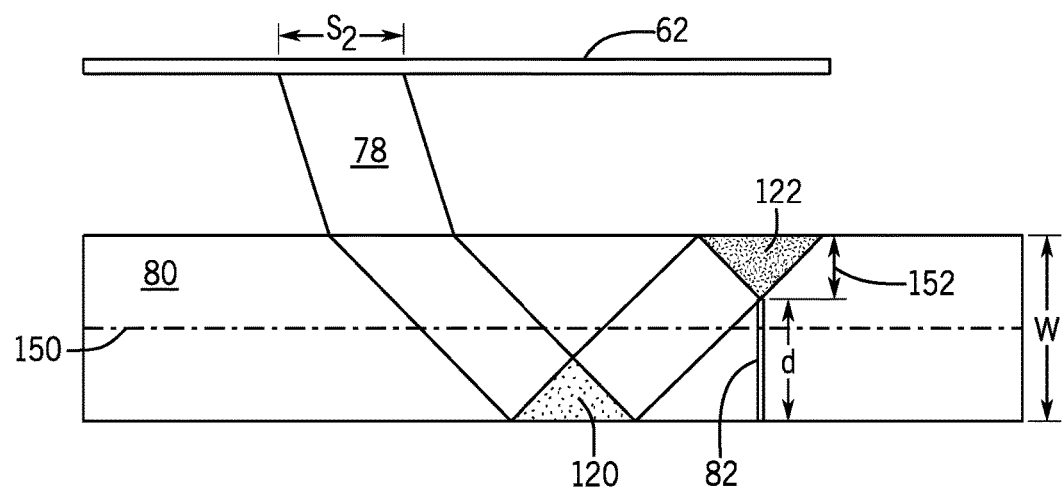
FIG. 5 is a schematic of one embodiment of the coverage areas for the transducer elements of FIG. 3 having a second effective width, $s_2$.

The techniques described above may be used to determine whether the feature 82 depth, d, exceeds a threshold value, $d_{min}$, which corresponds to the coverage areas 120, 122, but not the actual depth of the feature 82. As evidenced by Equations 1-6, the sizes of the coverage areas 120, 122 for a pipeline wall 80 having a given wall thickness, w, are a function of the width of the transducer elements, s. Accordingly, by increasing or decreasing number of transducer elements being utilized, the effective transducer width, s, may vary, causing the coverages areas 120, 122 to shrink or expand. FIGS. 4 and 5 illustrate how different effective transducer widths, s, result in differently sized coverage areas 120, 122.

FIG. 4 is a schematic of one embodiment of the coverage areas for the transducer elements 62 having a first effective width, $s_1$. As illustrated, the transducer elements 62 emit the ultrasonic signal 78 into the pipeline wall 80 having the thickness, w. Each of the coverage areas 120, 122 extends into the wall, past a center line 150, which represents a cylindrical plane extending axially through the middle of the pipeline wall 80. In the illustrated embodiment, the coverage areas 120, 122 extend into the pipeline wall 80 substantially the same distance as the depth, d, of the feature 82.

Similarly, FIG. 5 is a schematic of one embodiment of the coverage areas for the transducer elements 62 having a second effective width, $s_2$. As illustrated, the transducer elements 62 emit the ultrasonic signal 78 into the pipeline wall 80 having the thickness, w. Each of the coverage areas 120, 122 illustrated in FIG. 4 extends into the pipeline wall 80, but does not reach the center line 150. The coverage areas 120, 122 illustrated in FIG. 5 extend into the pipeline wall 80 substantially the same distance the remaining wall (i.e., the wall thickness, w, minus the feature depth, d). Because each skid 60 includes an array of transducer elements 62 (see FIG. 1) the effective transducer width, s, may be adjusted by utilizing various numbers (e.g., subsets) of the available transducer elements 62 within the array. For example, to achieve a desired effective transducer width, s, the system may utilize 8, 12, 16, 20, 24, 28, 32, or some other number, of the transducer elements 62 to emit the ultrasonic signal 78, where the number of transducer elements 62 utilized corresponds to the desired effective transducer width, s. By utilizing a subset of the transducer elements 62 of the array of transducer elements 62 on each skid 60 as the pig 10 moves through the pipeline 12, the effective transducer width, s, may be dynamically adjusted to effectuate adjustment of the coverage areas 120, 122.

In one embodiment, the pig 10 may move through the pipeline 12 utilizing a first number (e.g., first subset) of transducer elements 62 having an effective transducer width, $s_1$, resulting in coverage areas 120, 122 that enable detection of features 82 having a depth, d, greater than a threshold value, $d_{min}$. For example, a customer may desire to know of features having a depth, d, greater than 7 mm. Thus, the pig 10 may utilize the first subset of transducer elements 62 having the effective transducer width, $s_1$, that detects the presence of features 82 having a depth, d, greater than 7 mm. This amounts to a "coarse" shot. The processor 46 of the may analyze data in real time or near real time as the pig 10 moves through the pipeline 12. If the processor 46 of the control module 16 determines that a feature 82 having a depth, d, greater than the threshold value, $d_{min}$, (e.g., 7 mm) has been detected, the control module may change the number of transducer elements 62 utilized (e.g., second subset), adjusting the effective transducer width, s, to the second effective transducer width, $s_2$, in order to determine the depth, d, of the feature 82. These supplemental shots amount to a "fine" shot.

Because each skid 60 may be long compared to the width of each transducer element 62 and contain many transducer elements 62, the pig may be able to take a coarse shot of a section of pipe by emitting a first ultrasonic signal 78 (see, e.g., FIG. 4) from a first subset of sensors 62, recognize the presence of a feature 82, then emit a second ultrasonic signal 78 (see, e.g., FIG. 5) from a second subset of sensors 62 to determine the depth, d, of the feature 82. This may be done as the pig 10 moves continuously through the pipeline. For example, each skid 60 may include an array of sensors 62 that may be 200 or more sensors 62 long. The first coarse shot ultrasonic signal 78 may be generated using the first subset of transducer elements 62 near a downstream end 28 of the skid 60, while the second fine shot ultrasonic signal 78 may be generated using a second subset of transducer elements 62 upstream from the first subset of transducer elements 62. Performing coarse shots until a feature 82 is recognized and then adding supplemental fine shots can reduce the amount of data produced and the processing power to process the collected data relative to a system that does only fine shots. In some embodiments, only one additional fine shot may be performed to determine the depth, d, of the feature 82. In other embodiments, multiple additional fine shots may be performed, fine tuning the effective transducer width, s, by adjusting the number of transducer elements 62 utilized, in order to determine the depth, d, of the feature 82.

Figure 6:
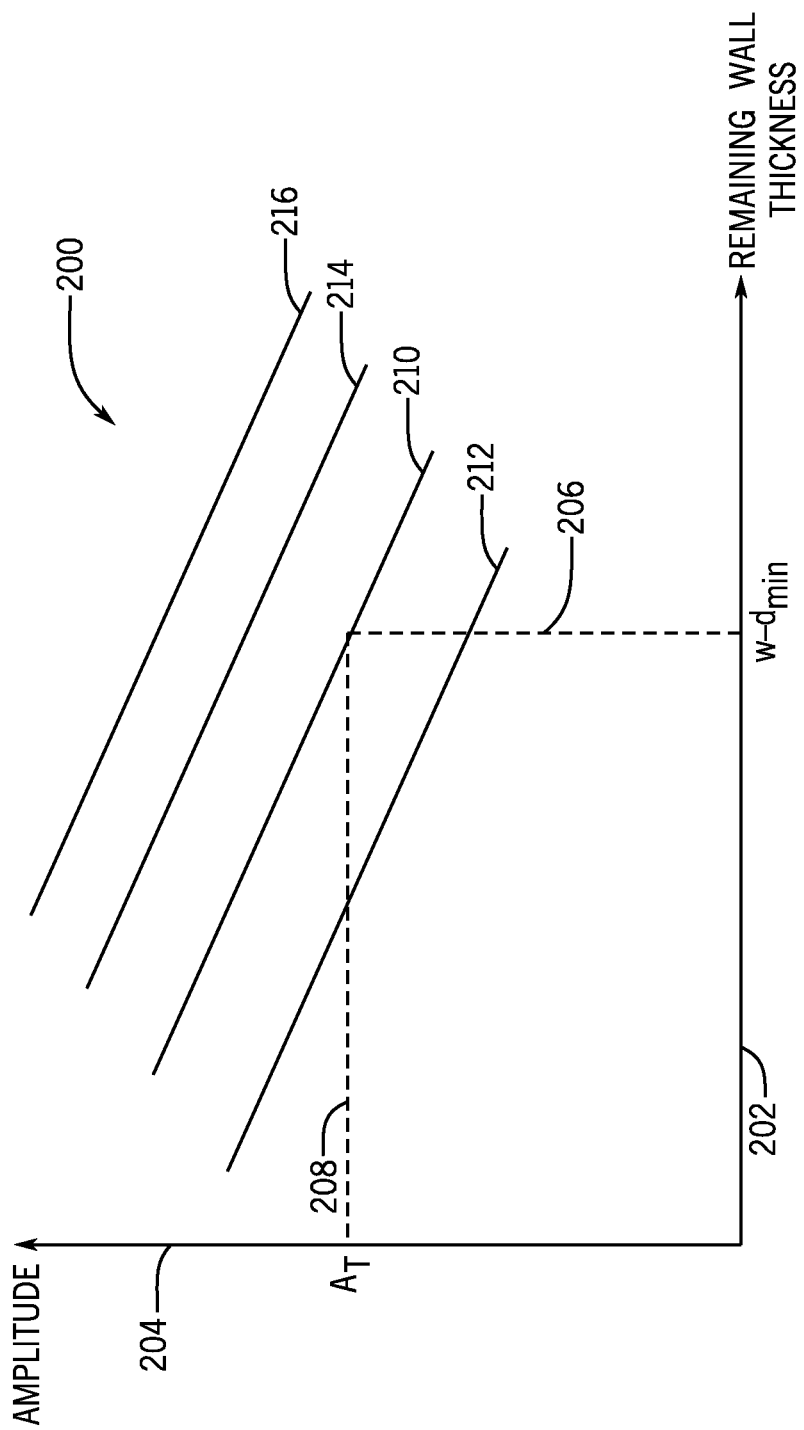
FIG. 6 is a graph that illustrates how to select the number of transducer elements of FIG. 3 to be utilized for a fine shot.

FIG. 6 is a graph 200 that illustrates a possibility for how to select the number of transducer elements 62 to be utilized for the fine shot discussed above. The horizontal axis 202 of graph 200 represents the remaining wall depth 152 and the vertical axis 204 of graph 200 represents the threshold amplitude, $A_T$. The remaining wall depth 152 may be determined by subtracting the threshold feature depth, $d_{min}$, which in some instances may be set by the customer or a user from the wall thickness, w, of the pipeline 12. For example, if a customer or user is interested in features 82 extending deeper than 3 mm and the pipe wall thickness, w, is 7.3 mm, then the remaining wall depth is 4.3 mm. If the wall thickness, w, of the pipeline 12 and the threshold feature depth, $d_{min}$, are substantially constant for a length of pipeline 12, these values may be determined before the pig 10 begins moving through the pipeline 12. Even in instances in which the wall thickness, w, changes between sections of pipeline across a run, these transitions in wall thickness may be accounted for ahead of time and the threshold feature depth, $d_{min}$, may be determined before the pipeline pig 10 moves through the pipeline.

The threshold amplitude, $A_T$, is the amplitude (e.g., in dB) above which a feature 82 is determined to exist. The threshold amplitude, $A_T$, may be determined experimentally based on a number of factors (e.g., pipe steel grade, medium, attenuation used). For example, the threshold amplitude, $A_T$, may be determined experimentally and a lookup table created such that a user or the processor 46 may determine the threshold amplitude, $A_T$, based on one or more known variables. Based on the remaining wall depth 152 and the threshold amplitude, $A_T$, the number of transducer elements 62 for a fine shot may be determined. For example, in the embodiment shown, the remaining wall depth 152, indicated by line 206, and the threshold amplitude, $A_T$, indicated by line 208, intersect at or near line 210, suggesting that the second subset should utilize 24 transducer elements for a fine shot. In other embodiments, the appropriate number of transducer elements 62 for a fine shot may be 20 transducer elements (line 212), 28 transducer elements (line 214), 32 transducer elements (line 216), or some other number of transducer elements. It should be understood that graph 200 is merely an example and that similar graphs for determining the number of transducer elements to be utilized in a fine shot may vary from embodiment to embodiment.

Figure 7:
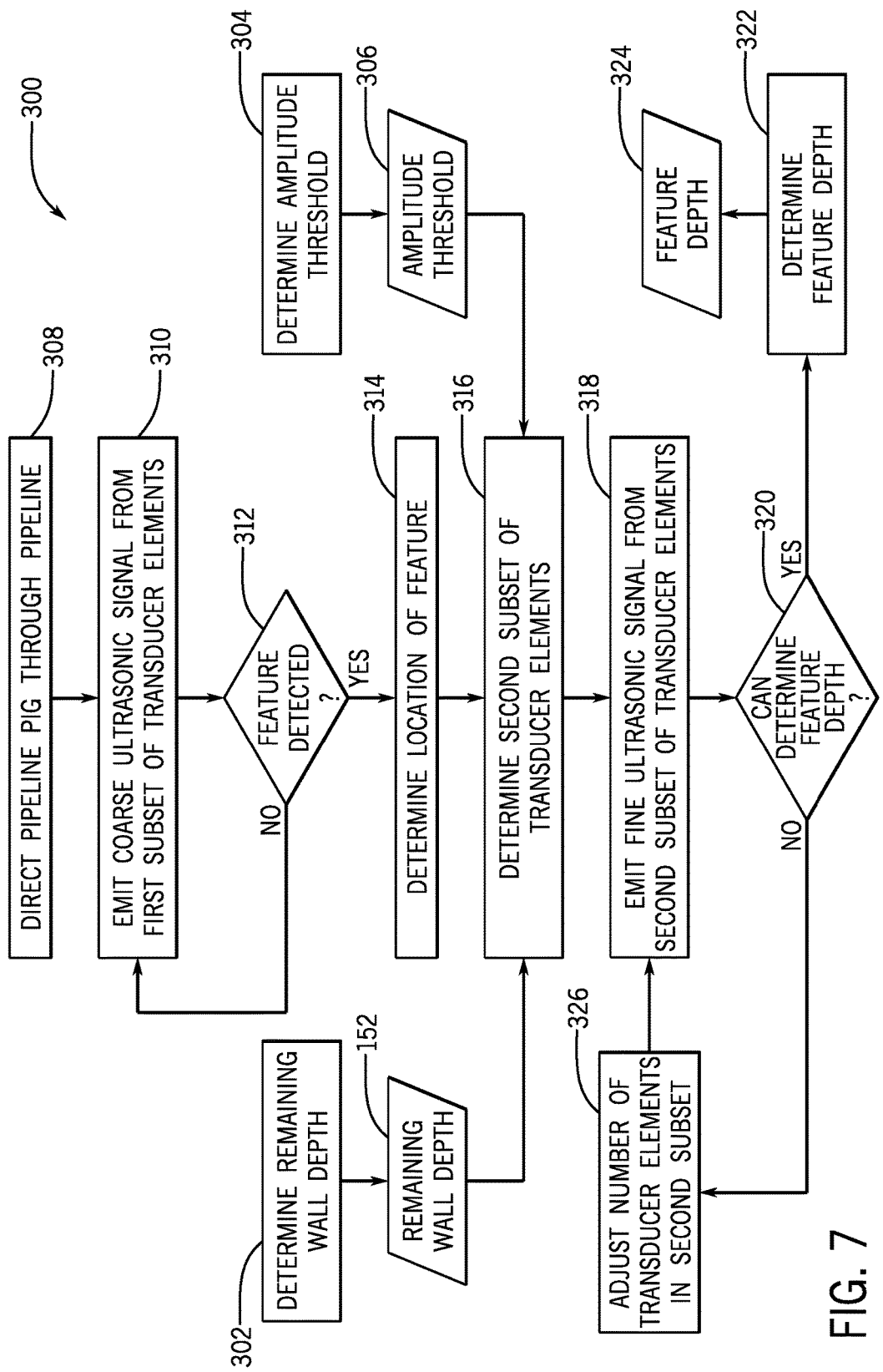
FIG. 7 is a flow chart of a process for determining a depth of the feature within the wall of the pipeline of FIG. 1.

FIG. 7 is a flow chart of a process 300 for determining the depth of a feature 82 within a wall 80 of a section of pipeline 12. In block 302 the remaining wall depth 152 may be determined based on the threshold feature depth, $d_{min}$, set by a user or a customer and the wall thickness, w, of the pipeline. As previously discussed the remaining wall depth 152 may be determined before the pig 10 is moved through the pipeline 12. In block 304, the amplitude threshold 306, $A_T$, may be determined and output. For example, the amplitude threshold 306, $A_T$, may be determined by the processor 46 using a lookup table stored in memory 48 based on one or more variables.

In block 308, the pipeline pig 12 may be directed through the pipeline 12. For example, the pig 10 may be propelled through a section of pipeline 12 by a difference between the pressure P1 ahead of the pig 10 and the pressure P2 behind the pig 10, as maintained by, for example, the plurality of sealing members 40. The pig 10 may pass through the section of pipeline 12 based upon the pressure of a fluid flowing through the pipeline 12 or based upon fluid pressure using a pump in an upstream direction 30 or downstream direction 28 of the pig 10.

In block 310 a coarse ultrasonic signal 78 is emitted from a first subset of transducer elements 62 selected by the processor 46. Echoes from the ultrasonic signal 78 propagating through the pipeline wall 80 and reflecting back toward the transducer elements 62 may be received and analyzed (e.g., by the processor 46 of the control module 16). At decision 312, the processor 46 of the control module 16 determines whether or not a feature 82 has been detected based on analysis of the collected data. If a feature 82 has not been detected, the processor may instruct the pig 10 to continue emitting coarse ultrasonic signals, as set forth on block 310. If a feature 82 has been detected, the pig 10 proceeds to block 314. At block 314, the processor 46 of the control module 16 determines the location of the feature 82.

At block 316, the processor 46 of the control module 16 determines a second subset of transducer elements 62 based on the remaining wall depth 152 and the amplitude threshold 306. For example, in some embodiments, the number of transducer elements 62 may be determined using a chart or a lookup table, as described with regard to FIG. 6. In block 318 a fine ultrasonic signal 78 is emitted from the second subset of transducer elements 62 at or near the feature 82 location determined in block 314. Echoes from the ultrasonic signal 78 propagating through the pipeline wall 80 and reflecting back toward the transducer elements 62 may be received and analyzed (e.g., by the processor 46 of the control module 16). At decision 320, the processor 46 of the control module 16 determines whether or not the feature 82 depth, d, can be determined based on the collected data. If the feature 82 depth, d, can be determined, the processor 46 of the control module 16 determines the feature depth, d, (block 322) and outputs the feature depth, d, 324. In some embodiments, the feature depth, d, 324 may be determined in post processing. If the processor 46 of the control module 16 determines that the feature depth, d, cannot be determined, the pig 10 proceeds to block 326 and adjusts the number of transducer elements 62 in the second subset of transducer elements 62. The pig 10 then proceeds to block 318 and emits another fine ultrasonic signal 78 from the adjusted second subset of transducer elements 62. In some embodiments, additional data processing (e.g., post-processing) may take place off-line after the data has been collected. For example, a user may utilize the computer 64 subsequent to a period of time passage, such as minutes, hours, days, weeks, or months after data has been collected to perform additional analysis of the collected data.

The disclosed techniques may be used to determine the depth of features, and in some cases, deep features 82 within a wall 80 of a pipeline 12. A pipeline pig 10 having a plurality of skids 60, each equipped with an array of ultrasonic transducer elements 62, can proceed through a section of pipeline 12. The pipeline pig 10 can utilize a first subset of transducer elements 62 to emit a coarse ultrasonic signal 78 into the wall 80 of the pipeline 12. Based on echoes sensed from the ultrasonic signals propagating through and reflecting within the wall 80 of the pipeline 12, the pig 10 can detect features within the wall 80 of the pipeline 12. The pig 10 may then emit one or more fine ultrasonic signals 78 from a second subset of the ultrasonic transducer elements 62. Based on the echoes of the fine ultrasonic signal sensed by the transducer elements 62, a depth of the feature 82 may be determined. Using a coarse and a fine ultrasonic signal can prevent the system 10 from being overloaded with data and also can make efficient use of the available processing power on the pig 10, enabling real time, or near real time, data analysis. Once the depth of one or more features have been determined, determinations as to the condition of the pipeline 12 may be made. For features with a depth large enough to warrant repair, plans may be made regarding when and how to repair the feature.

This written description uses examples to describe the disclosed subject matter, including the best mode, and also to enable any person skilled in the art to practice the invention, including making and using any devices or systems and performing any incorporated methods. The patentable scope of the disclosed subject matter is defined by the claims, and may include other examples that occur to those skilled in the art.

In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The invention claimed is:

1. A pipeline inspection system, comprising:
   a pipeline pig, comprising:
      a plurality of ultrasonic transducer elements situated in an array, wherein each of the plurality of ultrasonic transducer elements is configured to emit an ultrasonic signal into a wall of a pipeline and to receive echoes of the ultrasonic signal from the pipeline wall; and
      a controller configured to:
         select a first subset of the plurality of ultrasonic transducer elements from which to emit first ultrasonic signals into the wall of the pipeline as the pipeline pig passes through the pipeline;
         analyze the echoes of the first ultrasonic signals received by the plurality of ultrasonic transducer elements to detect a feature in the pipeline wall; and
         select a second subset of the plurality of ultrasonic transducer elements to emit second ultrasonic signals into the wall of the pipeline as the pipeline pig passes through the pipeline when the feature is detected in the pipeline wall;
      wherein the controller is configured to adjust a number of ultrasonic transducer elements in the second subset of the plurality of ultrasonic transducer elements if the depth of the feature cannot be determined based at least in part on the echoes of the second ultrasonic signals emitted by the second subset of ultrasonic transducer elements.

2. The pipeline inspection system of claim 1, wherein the second subset of the plurality of ultrasonic transducer elements is selected based on a remaining wall depth of the pipeline wall and a threshold value of an amplitude.

3. The pipeline inspection system of claim 2, wherein the controller is configured to determine the remaining wall depth by subtracting a threshold feature depth from a thickness of the pipeline wall.

4. The pipeline inspection system of claim 2, wherein the controller is configured to determine the amplitude threshold based on a lookup table.

5. The pipeline inspection system of claim 1, wherein the controller is configured to determine a depth of the feature based at least in part on the echoes of the second ultrasonic signals emitted by the second subset of ultrasonic transducer elements.

6. The pipeline inspection system of claim 1, wherein the pipeline pig comprises:
   a sensor carrier module comprising the plurality of transducer elements; and
   a control module comprising the controller, wherein the sensor carrier module and the control module are coupled to one another by a linkage.

7. The pipeline inspection system of claim 6, wherein the sensor carrier module comprises a plurality skids disposed circumferentially about the sensor carrier module, wherein at least one of the plurality of skids comprises the array of ultrasonic transducer elements.

8. The pipeline inspection system of claim 1, comprising a computing device for post-processing data collected by the pipeline pig.

9. A method, comprising:
directing a plurality of ultrasonic transducer elements situated in an array along a wall of a pipeline;
emitting a first ultrasonic signal from a first subset of the plurality of ultrasonic transducer elements;
receiving echoes of the first ultrasonic signal from the pipeline wall;
analyzing the echoes of the first ultrasonic signal to detect a feature in the pipeline wall;
emitting a second ultrasonic signal from a second subset of the plurality of ultrasonic transducer elements;
analyzing the echoes of the second ultrasonic signal to determine a depth of the feature in the pipeline wall; and
emitting a third ultrasonic signal from a third subset of the plurality of ultrasonic transducer elements when the depth of the feature in the pipeline wall cannot be determined based on the echoes of the second ultrasonic signal.

10. The method of claim 9, wherein the first subset of the plurality of ultrasonic transducer elements comprises a greater number of ultrasonic transducer elements relative to the second subset of the plurality of ultrasonic transducer elements.

11. The method of claim 9, wherein the second subset of the plurality of ultrasonic transducer elements is selected based on a remaining wall depth and an amplitude threshold.

12. The method of claim 11, wherein the remaining wall depth is determined by subtracting a threshold feature depth from a thickness of the pipeline wall, and wherein the amplitude threshold is determined based on a lookup table.

13. The method of claim 9, comprising post-processing data collected from the plurality of transducer elements using a computing device.

14. A non-transitory computer readable medium comprising executable instructions that when executed cause a processor to:

select a first subset of a plurality of ultrasonic transducer elements situated in an array, wherein the first subset of the plurality of ultrasonic transducer elements are configured to emit a first ultrasonic signal into a wall of a pipeline and to receive echoes of the first ultrasonic signal from the pipeline wall;

analyze the echoes of the first ultrasonic signal received by the first subset of the plurality of ultrasonic transducer elements to detect a feature in the pipeline wall;

select a second subset of the plurality of ultrasonic transducer elements, wherein the second subset of the plurality of ultrasonic transducer elements are configured to emit a second ultrasonic signal into the wall of the pipeline and to receive echoes of the second ultrasonic signal from the pipeline wall;

analyze the echoes of the second ultrasonic signal to determine a depth of the feature in the pipeline wall, and select a third subset of the plurality of ultrasonic transducer elements if the depth of the feature in the pipeline wall cannot be determined based on the echoes of the second ultrasonic signal, wherein the third subset of the plurality of ultrasonic transducer elements are configured to emit a third ultrasonic signal into the wall of the pipeline and to receive echoes of the third ultrasonic signal from the pipeline wall.

15. The non-transitory computer readable medium of claim 14, wherein the second subset of the plurality of ultrasonic transducer elements is selected based on a remaining wall depth and an amplitude threshold, wherein the remaining wall depth is determined by subtracting a threshold feature depth from a thickness of the pipeline wall, and wherein the amplitude threshold is determined based on a lookup table.

16. The non-transitory computer readable medium of claim 14, wherein the first subset of the plurality of ultrasonic transducer elements comprises a greater number of ultrasonic transducer elements relative to the second subset of the plurality of ultrasonic transducer elements.

17. The non-transitory computer readable medium of claim 14, wherein the non-transitory computer readable medium is disposed within a control module of a pipeline pig.

* * * * *